United States Patent
Yamada et al.

(10) Patent No.: US 9,743,666 B2
(45) Date of Patent: *Aug. 29, 2017

(54) HERBICIDAL COMPOSITION COMPRISING FLAZASULFURON AND AN INHIBITOR OF PROTOPORPHYRINOGEN OXIDASE

(71) Applicant: ISHIHARA SANGYO KAISHA, LTD., Osaka (JP)

(72) Inventors: Ryu Yamada, Shiga (JP); Hiroyuki Okamoto, Shiga (JP); Takashi Terada, Shiga (JP)

(73) Assignee: ISHIHARA SANGYO KAISHA, LTD., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/204,566

(22) Filed: Jul. 7, 2016

(65) Prior Publication Data

US 2016/0360754 A1    Dec. 15, 2016

Related U.S. Application Data

(62) Division of application No. 14/110,209, filed as application No. PCT/JP2012/060090 on Apr. 6, 2012, now Pat. No. 9,415,057.

(30) Foreign Application Priority Data

Apr. 11, 2011  (JP) ................................ 2011-087546

(51) Int. Cl.

| | | |
|---|---|---|
| A01N 43/54 | (2006.01) | |
| A01N 47/36 | (2006.01) | |
| A61K 31/7042 | (2006.01) | |
| A61K 31/7068 | (2006.01) | |
| A61K 31/7072 | (2006.01) | |
| C07H 19/10 | (2006.01) | |
| C07H 19/11 | (2006.01) | |
| C07H 19/207 | (2006.01) | |
| C07H 19/213 | (2006.01) | |
| A01N 43/56 | (2006.01) | |
| A01N 43/653 | (2006.01) | |
| A01N 43/76 | (2006.01) | |
| A01N 43/82 | (2006.01) | |
| A01N 43/84 | (2006.01) | |
| A01N 43/90 | (2006.01) | |

(52) U.S. Cl.
CPC .............. *A01N 47/36* (2013.01); *A01N 43/54* (2013.01); *A01N 43/56* (2013.01); *A01N 43/653* (2013.01); *A01N 43/76* (2013.01); *A01N 43/82* (2013.01); *A01N 43/84* (2013.01); *A01N 43/90* (2013.01); *A61K 31/7042* (2013.01); *A61K 31/7068* (2013.01); *A61K 31/7072* (2013.01); *C07H 19/10* (2013.01); *C07H 19/11* (2013.01); *C07H 19/207* (2013.01); *C07H 19/213* (2013.01)

(58) Field of Classification Search
None
See application file for complete search history.

(56) References Cited

U.S. PATENT DOCUMENTS

| | | |
|---|---|---|
| 7,375,058 B2 | 5/2008 | Zagar et al. |
| 8,575,067 B2 | 11/2013 | Yoshii et al. |
| 8,921,271 B2 | 12/2014 | Yamada et al. |
| 9,415,057 B2 * | 8/2016 | Yamada ............ A01N 47/36 |
| 2002/0004457 A1 * | 1/2002 | Nevill ............. A01N 61/00 504/138 |
| 2008/0132414 A1 | 6/2008 | Zawierucha et al. |
| 2009/0069346 A1 * | 3/2009 | Ishihara ........... A01N 47/36 514/256 |

FOREIGN PATENT DOCUMENTS

| | | |
|---|---|---|
| DE | 19933702 | 11/1999 |
| JP | 2005-68121 | 3/2005 |
| WO | 00/27203 | 5/2000 |
| WO | 03/024221 | 3/2003 |
| WO | 2007/105377 | 9/2007 |

OTHER PUBLICATIONS

Jhala et al., "Herbicide Tank Mixtures for Broad-Spectrum Weed Control in Florida Citrus", Weed Technology, vol. 27, 2013, pp. 129-137.
Waggoner et al., "Control of Glyphosate-Resistant Horseweed (Conyza Canadensis) with Saflufenacil Tank Mixtures in No-Till Cotton", Weed Technology, vol. 25, 2011, pp. 310-315.
Japanese Office Action with English translation in respect to Japanese Application No. 2012-083673, issued Dec. 22, 2015.
International Search Report for International Application No. PCT/JP2012/060090, dated Jul. 2, 2012.
"Weeds", Colby S.R., vol. 15, pp. 20-22, 1967.
U.S. Appl. No. 14/110,289, filed Oct. 7, 2013.
International Preliminary Report on Patentability for International Patent Application No. PCT/JP2012/060090, dated Oct. 24, 2013.

* cited by examiner

*Primary Examiner* — Alton Pryor
(74) *Attorney, Agent, or Firm* — Greenblum & Bernstein, P.L.C.

(57) ABSTRACT

Many herbicidal compositions have been developed and are presently used. However, weeds to be controlled are various in types and their emergence extends over a long period. Accordingly, it is desired to develop a herbicidal composition which has a broad herbicidal spectrum, a high activity and a long-lasting effect.

The present invention provides a herbicidal composition comprising (A) flazasulfuron or its salt and (B) at least one protoporphyrinogen oxidase inhibitor selected from the group consisting of a phenylpyrazole compound, a triazolinone compound, a N-phenylphthalimide compound, a pyrimidindione compound, an oxadiazole compound, an oxazolidinedione compound, a thiadiazole compound, pyraclonil, profluazol, flufenpyr-ethyl and their salts. According to the present invention, a herbicidal composition which has a broad herbicidal spectrum, a high activity and a long-lasting effect can be provided.

6 Claims, No Drawings

HERBICIDAL COMPOSITION COMPRISING FLAZASULFURON AND AN INHIBITOR OF PROTOPORPHYRINOGEN OXIDASE

CROSS-REFERENCE TO RELATED APPLICATIONS

The present application is a Divisional of U.S. application Ser. No. 14/110,209, which is a national stage of international patent application no. PCT/JP2012/060090, filed Apr. 6, 2012, which claims priority of JP 2011-087546, filed Apr. 11, 2011. The entire disclosures of these applications are expressly incorporated by reference herein.

TECHNICAL FIELD

The present invention relates to a herbicidal composition comprising flazasulfuron or its salt and a protoporphyrinogen oxidase inhibitor.

BACKGROUND ART

Various herbicidal compositions have been studied to control undesired plants (hereinafter sometimes referred to simply as "weeds") in agricultural fields and non-agricultural fields.

For example, Patent Document 1 discloses microgranules comprising a compound which inhibits protoporphyrinogen oxidase when absorbed from the stem and leaves, a photosynthesis inhibiting herbicide and an acetolactate synthase inhibiting herbicide, which are to be directly applied to plants to be controlled. Patent Documents 2 and 3 also disclose various herbicidal compositions, and as one example, a combination of a protoporphyrinogen oxidase inhibitor and an acetolactate synthase inhibiting herbicide is disclosed.

However, a herbicidal composition comprising flazasulfuron or its salt and a protoporphyrinogen oxidase inhibitor is not disclosed in any of Patent Documents 1 to 3.

Prior Art Documents

Patent Documents

Patent Document 1: JP-A-2005-68121
Patent Document 2: WO2003/024221
Patent Document 3: WO00/27203

DISCLOSURE OF INVENTION

Technical Problem

Many herbicidal compositions have been developed and are presently used, but as weeds to be controlled are many in types and their emergence extends over a long period, it is desired to develop a herbicidal composition having a broader herbicidal spectrum, a high activity and a long-lasting effect.

Solution to Problem

It is possible to provide a herbicidal composition having a broader herbicidal spectrum, a high activity and a long-lasting effect, by use of flazasulfuron or its salt and a specific protoporphyrinogen oxidase inhibitor in combination.

That is, the present invention provides a herbicidal composition comprising (A) flazasulfuron or its salt and (B) at least one protoporphyrinogen oxidase inhibitor selected from the group consisting of a phenylpyrazole compound, a triazolinone compound, a N-phenylphthalimide compound, a pyrimidindione compound, an oxadiazole compound, an oxazolidinedione compound, a thiadiazole compound, pyraclonil, profluazol, flufenpyr-ethyl and their salts. Further, the present invention provides a method for controlling undesired plants or inhibiting their growth, which comprises applying a herbicidally effective amount of the above herbicidal composition. The present invention further provides a method for controlling undesired plants or inhibiting their growth, which comprises applying herbicidally effective amounts of (A) and (B), to the undesired plants or to a place where they grow.

Advantageous Effects of Invention

The herbicidal composition of the present invention comprising flazasulfuron or its salt and a specific protoporphyrinogen oxidase inhibitor as active ingredients is capable of controlling a wide range of undesired plants in cropland or non-cropland, and it surprisingly presents a synergistic herbicidal effect i.e. a herbicidal effect higher than the mere addition of the respective herbicidal effects of the active ingredients, and it can be applied at a low dose as compared with a case where the respective active ingredients are applied individually. Such a herbicidal composition of the present invention has an enlarged herbicidal spectrum, and further its herbicidal effect will last over a long period of time.

When the herbicidal activity in a case where two active ingredients are combined, is larger than the simple sum of the respective herbicidal activities of the two active ingredients (the expected activity), it is called a synergistic effect. The activity expected by the combination of two active ingredients can be calculated as follows (Colby S. R., "Weed", vol. 15, p. 20-22, 1967).

$$E=\alpha+\beta-(\alpha\times\beta\div 100)$$

where α: growth inhibition rate when treated with x (g/ha) of herbicide X,
β: growth inhibition rate when treated with y (g/ha) of herbicide Y,
E: growth inhibition rate expected when treated with x (g/ha) of herbicide X and y (g/ha) of herbicide Y.

That is, when the actual growth inhibition rate (measured value) is larger than the growth inhibition rate by the above calculation (calculated value), the activity by the combination can be regarded as showing a synergistic effect. The herbicidal composition of the present invention shows a synergistic effect when calculated by the above formula.

DESCRIPTION OF EMBODIMENTS

The herbicidal composition of the present invention comprises, as active ingredients, (A) flazasulfuron or its salt (hereinafter sometimes referred to as "compound A") and (B) at least one protoporphyrinogen oxidase inhibitor selected from the group consisting of a phenylpyrazole compound, a triazolinone compound, a N-phenylphthalimide compound, a pyrimidindione compound, an oxadiazole compound, an oxazolidinedione compound, a thiadiazole compound, pyraclonil, profluazol, flufenpyr-ethyl and their salts (hereinafter they will sometimes be referred to as "compound B").

In the compound A, flazasulfuron (common name) is 1-(4,6-dimethoxypyrimidin-2-yl)-3-(3-trifluoromethyl-2-pyridylsulfonyl)urea.

The compound B will be described in detail below. The compound B is represented by common names.

The phenylpyrazole compound may, for example, be pyraflufen-ethyl or fluazolate. Among them, pyraflufen-ethyl is preferred.

The triazolinone compound may, for example, be azafenidin, bencarbazone, carfentrazone-ethyl or sulfentrazone. Among them, azafenidin, carfentrazone-ethyl or sulfentrazone is preferred, and carfentrazone-ethyl or sulfentrazone is more preferred.

The N-phenylphthalimide compound may, for example, be cinidon-ethyl, flumiclorac-pentyl or flumioxazin. Among them, flumioxazin or flumiclorac-pentyl is preferred, and flumioxazin is more preferred.

The pyrimidindione compound may, for example, be benzfendizone, butafenacil, saflufenacil or ethyl [3-(2-chloro-4-fluoro-5-(3-methyl-2,6-dioxo-4-trifluoromethyl-3,6-dihydro-2H-pyrimidin-1-yl)phenoxy)pyridin-2-yloxy]acetate (test code: SYN-523). Among them, butafenacil or saflufenacil is preferred.

The oxadiazole compound may, for example, be oxadiargyl or oxadiazon. Among them, oxadiargyl is preferred.

The oxazolidinedione compound may, for example, be pentoxazone.

The thiadiazole compound may, for example, be fluthiacet-methyl or thidiazimin. Among them, fluthiacet-methyl is preferred.

Other compounds included in the compound B may, for example, be pyraclonil, profluazol and flufenpyr-ethyl. Among them, pyraclonil or flufenpyr-ethyl is preferred.

The compound B is preferably the phenylpyrazole compound, the triazolinone compound, the N-phenylphthalimide compound, the pyrimidindione compound or the oxadiazole compound, more preferably the phenylpyrazole compound, the triazolinone compound or the N-phenylphthalimide compound, capable of achieving a high herbicidal effect when combined with the compound A.

More specifically, preferred is pyraflufen-ethyl, carfentrazone-ethyl, sulfentrazone, flumioxazin, saflufenacil, ethyl [3-(2-chloro-4-fluoro-5-(3-methyl-2,6-dioxo-4-trifluoromethyl-3,6-dihydro-2H-pyrimidin-1-yl)phenoxy)pyridin-2-yloxy]acetate (test code: SYN-523), oxadiargyl, fluthiacet-methyl, flufenpyr-ethyl, flumiclorac-pentyl, azafenidin, butafenacil, pentoxazone or pyraclonil, and more preferred is pyraflufen-ethyl, carfentrazone-ethyl, sulfentrazone, flumioxazin, saflufenacil, oxadiargyl, fluthiacet-methyl, flufenpyr-ethyl, butafenacil, pentoxazone or pyraclonil.

The salt included in the compound A or the compound B may be any salt so long as it is agriculturally acceptable. Examples thereof include alkali metal salts such as a sodium salt and a potassium salt; alkaline earth metal salts such as a magnesium salt and a calcium salt; ammonium salts such as a monoethylammonium salt, a dimethylammonium salt and a triethylammonium salt; inorganic acid salts such as a hydrochloride, a perchlorate, a sulfate and a nitrate, and organic acid salts such as an acetate and a methanesulfonate.

The mixing ratio of the compound A to the compound B cannot generally be defined, as it may vary depending upon various conditions such as the type of the formulation, the weather conditions, and the type and the growth stage of the undesired plants to be controlled, but it is preferably a mixing ratio to achieve the herbicidally effective amounts (synergistic herbicidally effective amount) with which the synergistic herbicidal effect is obtained, and for example, by the weight ratio, it is preferably from 100:1 to 1:100, more preferably from 50:1 to 1:64, particularly preferably from 20:1 to 1:32.

When pyraflufen-ethyl is used as the compound B, the mixing ratio of the compound A to the compound B is, for example, by the weight ratio, preferably from 20:1 to 1:8, more preferably from 20:1 to 1:3.2.

When carfentrazone-ethyl is used as the compound B, the mixing ratio of the compound A to the compound B is, for example, by the weight ratio, preferably from 40:1 to 1:40, more preferably from 20:1 to 1:18, particularly preferably from 5:1 to 1:18.

When sulfentrazone is used as the compound B, the mixing ratio of the compound A to the compound B is, for example, by the weight ratio, preferably from 10:1 to 1:50, more preferably from 4:1 to 1:25, particularly preferably from 2:1 to 1:20.

When flumioxazin is used as the compound B, the mixing ratio of the compound A to the compound B is, for example, by the weight ratio, preferably from 100:1 to 1:75, more preferably from 50:1 to 1:24, particularly preferably from 20:1 to 1:20.

When saflufenacil is used as the compound B, the mixing ratio of the compound A to the compound B is, for example, by the weight ratio, preferably from 20:1 to 1:10, more preferably from 10:1 to 1:8.

When oxadiargyl is used as the compound B, the mixing ratio of the compound A to the compound B is, for example, by the weight ratio, preferably from 2:1 to 1:100, more preferably from 1:1 to 1:32.

When fluthiacet-methyl is used as the compound B, the mixing ratio of the compound A to the compound B is, for example, by the weight ratio, preferably from 20:1 to 1:10, more preferably from 10:1 to 1:2.

When flufenpyr-ethyl is used as the compound B, the mixing ratio of the compound A to the compound B is, for example, by the weight ratio, preferably from 20:1 to 1:10, more preferably from 10:1 to 1:2.

When butafenacil is used as the compound B, the mixing ratio of the compound A to the compound B is, for example, by the weight ratio, preferably from 20:1 to 1:25, more preferably from 5:1 to 1:8.

When pentoxazone is used as the compound B, the mixing ratio of the compound A to the compound B is, for example, by the weight ratio, preferably from 2:1 to 1:50, more preferably from 0.5:1 to 1:10.

When pyraclonil is used as the compound B, the mixing ratio of the compound A to the compound B is, for example, by the weight ratio, preferably from 2:1 to 1:50, more preferably from 0.5:1 to 1:10.

The doses of the compound A and the compound B cannot generally be defined, as they may vary depending upon various conditions such as the mixing ratio of the compound A to the compound B, the type of the formulation, the weather conditions, and the type and the growth stage of the undesired plants to be controlled. However, they are preferably doses to achieve the herbicidally effective amounts (synergistic herbicidally effective amount) with which the synergistic herbicidal effect is obtained, and for example, the dose of the compound A is preferably from 0.5 to 120 g/ha, more preferably from 1 to 110 g/ha, particularly preferably from 1 to 100 g/ha, and the dose of the compound B is preferably from 0.5 to 1,000 g/ha, more preferably from 1 to 900 g/ha, particularly preferably from 2 to 800 g/ha.

With respect to the doses of the compounds A and B when pyraflufen-ethyl is used as the compound B, for example, the dose of the compound A is preferably from 0.5 to 120 g/ha, more preferably from 1 to 110 g/ha, particularly preferably from 1 to 100 g/ha, and the dose of the compound B is preferably from 1 to 100 g/ha, more preferably from 1 to 90 g/ha, particularly preferably from 2 to 80 g/ha.

With respect to the doses of the compounds A and B when carfentrazone-ethyl is used as the compound B, for example, the dose of the compound A is preferably from 0.5 to 120 g/ha, more preferably from 0.5 to 110 g/ha, particularly preferably from 1 to 100 g/ha, and the dose of the compound B is preferably from 2.5 to 400 g/ha, more preferably from 10 to 250 g/ha, particularly preferably from 10 to 50 g/ha.

With respect to the doses of the compounds A and B when sulfentrazone is used as the compound B, for example, the dose of the compound A is preferably from 10 to 100 g/ha, more preferably from 20 to 100 g/ha, particularly preferably from 25 to 100 g/ha, and the dose of the compound B is preferably from 10 to 500 g/ha, more preferably from 25 to 500 g/ha.

With respect to the doses of the compounds A and B when flumioxazin is used as the compound B, for example, the dose of the compound A is preferably from 10 to 100 g/ha, more preferably from 25 to 100 g/ha, particularly preferably from 25 to 50 g/ha, and the dose of the compound B is preferably from 1 to 750 g/ha, more preferably from 2 to 600 g/ha, particularly preferably from 2.5 to 500 g/ha.

With respect to the doses of the compounds A and B when saflufenacil is used as the compound B, for example, the dose of the compound A is preferably from 10 to 100 g/ha, more preferably from 12.5 to 100 g/ha, and the dose of the compound B is preferably from 5 to 100 g/ha.

With respect to the doses of the compounds A and B when oxadiargyl is used as the compound B, for example, the dose of the compound A is preferably from 10 to 100 g/ha, more preferably from 12.5 to 100 g/ha, and the dose of the compound B is preferably from 50 to 1,000 g/ha, more preferably from 150 to 800 g/ha.

With respect to the doses of the compounds A and B when fluthiacet-methyl is used as the compound B, for example, the dose of the compound A is preferably from 10 to 100 g/ha, more preferably from 25 to 50 g/ha, and the dose of the compound B is preferably from 5 to 100 g/ha, more preferably from 5 to 50 g/ha.

With respect to the doses of the compounds A and B when flufenpyr-ethyl is used as the compound B, for example, the dose of the compound A is preferably from 10 to 100 g/ha, more preferably from 25 to 50 g/ha, and the dose of the compound B is preferably from 5 to 100 g/ha, more preferably from 5 to 50 g/ha.

With respect to the doses of the compounds A and B when butafenacil is used as the compound B, for example, the dose of the compound A is preferably from 10 to 100 g/ha, more preferably from 12.5 to 50 g/ha, and the dose of the compound B is preferably from 5 to 250 g/ha, more preferably from 10 to 100 g/ha.

With respect to the doses of the compounds A and B when pentoxazone is used as the compound B, for example, the dose of the compound A is preferably from 10 to 100 g/ha, more preferably from 25 to 50 g/ha, and the dose of the compound B is preferably from 50 to 500 g/ha, more preferably from 100 to 250 g/ha.

With respect to the doses of the compounds A and B when pyraclonil is used as the compound B, for example, the dose of the compound A is preferably from 10 to 100 g/ha, more preferably from 25 to 50 g/ha, and the dose of the compound B is preferably from 50 to 500 g/ha, more preferably from 100 to 250 g/ha.

The herbicidal composition of the present invention may be applied to undesired plants or may be applied to a place where they grow. Further, it may be applied at any time either before or after the emergence of the undesired plants. Further, the herbicidal composition of the present invention may take various application forms such as soil application, foliar application, irrigation application, and submerged application, and it can be applied to agricultural fields such as upland fields, orchards and paddy fields, and non-crop-land such as ridges of fields, fallow fields, play grounds, golf courses, vacant lands, forests, factory sites, railway sides and roadsides.

The herbicidal composition of the present invention can control a broad range of undesired plants such as annual weeds and perennial weeds. The undesired plants to be controlled by the herbicidal composition of the present invention may, for example, be cyperaceae such as green kyllinga (*Kyllinga brevifolia* Rottb. var. leiolepis), or sedge (*Cyperus* spp.) [the sedge may, for example, be purple nutsedge (*Cyperus rotundus* L.), smallflower umbrella sedge (*Cyperus difformis* L.), yellow nutsedge (*Cyperus esculentus* L.) or amur cyperus (*Cyperus microiria* Steud.)]; gramineae such as barnyardgrass (*Echinochloa crus-galli* L., *Echinochloa oryzicola* vasing.), japanese millet (*Echinochloa utilis* Ohwi et Yabuno), crabgrass (*Digitaria* spp.) [the crabgrass may, for example, be summergrass (*Digitaria ciliaris* (Retz.) Koel), large crabgrass (*Digitaria sanguinalis* L.), violet crabgrass (*Digitaria violascens* Link) or *Digitaria horizontalis* Willd.], green foxtail (*Setaria viridis* L.), giant foxtail (*Setaria faberi* Herrm.), goosegrass (*Eleusine indica* L.), johnsongrass (*Sorghum halepense* (L.) Pers.), bermudagrass (*Cynodon dactylon* (L.) Pers.), wild oat (*Avena fatua* L.), annual bluegrass (*Poa annua* L.), panic grass (*Panicum* spp.) [the panic grass may, for example, be guinea grass (*Panicum maximum* Jacq.), or fall panicum (*Panicum dichotomiflorum* (L.) Michx.)], signal grass (*Brachiaria* spp.) [the signal grass may, for example, be plantain signal grass (*Brachiaria plantaginea* (LINK) Hitchc.), palisade signal grass (*Brachiaria decumbens* Stapf), or mauritius signal grass (*Brachiaria mutica* (Forssk.) Stapf)], paspalum (*Paspalum* spp.), itchgrass (*Rottboellia cochinchinensis* (LOUR.) W. D. CLAYTON); southern sandbur (*Cenchrus echinatus* L.), or shattercane (*Sorghum bicolor* (L.) Moench.); scrophulariaceae such as persian speedwell (*Veronica persica* Poir.), or corn speedwell (*Veronica arvensis* L.); compositae such as beggar ticks (*Bidens* spp.) [the beggar ticks may, for example, be hairy beggarticks (*Bidens pilosa* L.), devils berggarticks (*Bidens frondosa* L.), *Bidens biternata* (Lour.) Merr. et Sherff), or beggarticks (*Bidens subalternans* DC.)], hairy fleabane (*Conyza bonariensis* (L.) Cronq.), horseweed (*Erigeron canadensis* L.), dandelion (*Taraxacum officinale* Weber), or common cocklebur (*Xanthium strumarium* L.); leguminosae such as rattlepod or rattlebox (*Crotalaria* spp.) [the rattlepod or rattlebox may, for example, be sunn-hemp (*Crotalaria juncea* L.)], poison bean (*Sesbania* spp.) [the poison bean may, for example, be rostrate sesbania (*Sesbania rostrata* Bremek. & Oberm.) or sesbania pea (*Sesbania cannabina* (Retz.) Pers.)], white clover (*Trifolium repens* L.); caryophyllaceae such as sticky chickweed (*Cerastium glomeratum* Thuill.), or common chickweed (*Stellaria media* L.); euphorbiaceae such as garden spurge (*Euphorbia hirta* L.), threeseeded copperleaf (*Acalypha australis* L.), or fireplant (*Euphorbia heterophylla* L.); plantaginaceae such as asiatic plantain (*Plantago asiatica* L.); oxalidaceae such as creeping woodsorrel (*Oxalis corniculata* L.); apiaceae such as lawn pennywort (*Hydrocotyle sibthorpioides* Lam.); violaceae such as violet (*Viola mandshurica* W. Becker); iridaceae such as blue-eyedgrass (*Sisyrinchium rosulatum* Bicknell); geraniaceae such as carolina *geranium* (*Geranium carolinianum* L.); labiatae such as purple deadnettle (*Lamium purpureum* L.), or henbit (*Lamium amplexicaule* L.); malvaceae such as velvetleaf (*Abutilon theophrasti* MEDIC.), or prickly *sida* (*Sida spinosa* L.); convolvulaceae such as ivy-leaved morningglory (*Ipomoea hederacea* (L.) Jacq.), common morningglory (*Ipomoea purpurea* ROTH), cypressvine morningglory (*Ipomoea quamoclit* L.), *Ipomoea grandifolia* (DAMMERMANN) O'DONNELL, hairy *merremia* (*Merremia aegvotia* (L.) URBAN), or field Bindweed (*Convolvulus arvensis* L.); chenopodiaceae such as common lambsquarters (*Chenopodium album* L.); portulacaceae such as common purslane (*Portulaca oleracea* L.); amaranthaceae such as pigweed (*Amaranthus* spp.) [the pigweed may, for example, be prostrate pigweed (*Amaranthus blitoides* S. Wats.), livid amaranth (*Amaranthus lividus* L.), purple amaranth (*Amaranthus blitum* L.), smooth pigweed (*Amaranthus hybridus* L.), *Amaranthus patulus* Bertol., powell amaranth (*Amaranthus powellii* S. Wats.), slender amaranth (*Amaranthus viridis* L.), palmer amaranth (*Amaranthus palmeri* S. Wats.), redroot pigweed (*Amaranthus retroflexus* L.), tall waterhemp (*Amaranthus tuberculatus* (Moq.) Sauer.), common waterhemp (*Amaranthus tamariscinus* Nutt.), thorny amaranth (*Amaranthus spinosus* L.), ataco (*Amaranthus quitensis* Kunth.), or *Amaranthus rudis* Sauer]; solanaceae such as black nightshade (*Solanum nigrum* L.); polygonaceeae such as spotted knotweed (*Polygonum lapathifolium* L.), or green smartweed (*Polygonum scabrum* MOENCH); cruciferae such as flexuous bittercress (*Cardamine flexuosa* WITH.); cucurbitaceae such as burcucumber (*Sicyos angulatus* L.); or commelinaceae such as common dayflower (*Commelina communis* L.); rosaceae such as mock strawberry (*Duchesnea chrysantha* (Zoll. et Mor.) Miq.); molluginacea such as carpetweed (*Mollugo verticillata* L.); or rubiaceae such as false cleavers (*Galium spurium* var. *echinospermon* (Wallr.) Hayek) or stickywilly (*Galium aparine* L.).

The herbicidal composition of the present invention can control even weeds against which the compound A has no satisfactory controlling effects depending upon various conditions such as the weather conditions, and the growth stage of the weeds. For example, the compound A has no satisfactory controlling effects against some weeds included in solanaceae, scrophulariaceae and gramineae in some cases depending upon various conditions such as the weather conditions and the growth stage of the weeds, however, the herbicidal composition of the present invention comprising the combination of the compounds A and B has excellent effect to control such weeds or to inhibit their growth.

Further, the herbicidal composition of the present invention can control perennial grass weeds such as quackgrass (*Agropyron repens* (L.) P. Beauv.), Cholorado bluestem (*Agropyron tsukushiense* (Honda) Ohwi var. *transiens* (Hack.) Ohwi), redtop (*Agrostis alba* L.), orchardgrass (*Dactylis glomerata* L.), perennial ryegrass (*Lolium perenne* L.), eulaliagrass (*Miscanthus sinensis* Anderss.), knotgrass (*Paspalum distichum* L.), bahiagrass (*Paspalum notatum* Flugge), johnsongrass (*Sorghum halepense* L.), bermuda grass (*Cynodon dactylon* (L.) Pers.), dallisgrass (*Paspalum dilatatum* Poir.), cogongrass (*Imperata cylindrica* (L.) Beauv.), japanese *paspalum* (*Paspalum thunbergii* Kunth) which are problematic as strong weeds in agricultural fields such as orchards and non-cropland such as golf courses, railway sides and roadsides. Further, the herbicidal composition of the present invention has a high herbicidal activity also against weeds in late leaf stage, such as weeds in 5-leaf stage to heading stage, and such is particularly remarkable for grass weeds. The herbicidal composition of the present invention has favorable herbicidal effects against grass weeds and broad leaf weeds either by foliar application or soil application.

Further, as one of cultivation manners for crop plants, different crop plants may be cultivated in the same field by differentiating timing for their cultivation. For example, in the same field where corn was cultivated last year, sugarcane may be cultivated this year, and in such a case, the previous crop plant such as the corn may be an object to be controlled as an undesired plant. Further, along with spread of genetically modified crop plants or increase of cultivation fields, there may be a case where at the time of repeated cultivation, rotational cropping or change in cropping, the previous crop plant grown as weeds (volunteer crop plant) becomes an object to be controlled as an undesired plant. Even in such a situation, the herbicidal composition of the present invention is capable of controlling the undesired plant to be controlled and thus is very useful in such a practical application.

Further, in practical application in which the rapid herbicidal efficacy and regrowth of the undesired plants after the herbicidal composition is applied are problematic, the herbicidal composition of the present invention is useful in view of the rapid herbicidal efficacy and a high effect of suppressing regrowth of the undesired plants.

The herbicidal composition of the present invention may further contain other herbicidal compounds in addition to the above-described active ingredients so long as such will meet the object of the present invention, and there may be a case where it is thereby possible to improve e.g. the range of undesired plants to be controlled, the timing for application of the herbicidal composition, the herbicidal activities, etc. to more desirable directions. Such other herbicidal compounds include, for example, the following compounds (common names including ones under application for approval by ISO, or test codes, here, "under application for approval by ISO" means common names before approval by ISO (International Organization for Standardization)), and one or more of them may suitably be selected for use. Even when not specifically mentioned here, in a case where such compounds have salts, alkyl esters, hydrates, different crystal forms, various structural isomers, etc., they are, of course, all included.

Further, in consideration of the application site of the herbicidal composition or the type or growth state of the undesired plants, the herbicidal composition of the present invention may be mixed with or may be used in combination with fungicides, antibiotics, plant hormones, insecticides, fertilizers, phytotoxicity-reducing agents, etc., whereby more excellent effects and activities may sometimes be obtained.

(1) Those which are believed to exhibit herbicidal effects by disturbing hormone activities of plants, such as a phenoxy type such as 2,4-D, 2,4-D-butotyl, 2,4-D-butyl, 2,4-D-dimethylammonium, 2,4-D-diolamine, 2,4-D-ethyl, 2,4-D-2-ethylhexyl, 2,4-D-isobutyl, 2,4-D-isoctyl, 2,4-D-isopropyl, 2,4-D-isopropylammonium, 2,4-D-sodium, 2,4-D-isopropanolammonium, 2,4-D-trolamine, 2,4-DB, 2,4-DB-butyl, 2,4-DB-dimethylammonium, 2,4-DB-isoctyl, 2,4-DB-potassium, 2,4-DB-sodium, dichlorprop, dichlorprop-butotyl, dichlorprop-dimethylammonium, dichlorprop-isoctyl, dichlorprop-potassium, dichlorprop-P, dichlorprop-P-dimethylammonium, dichlorprop-P-potassium, dichlorprop-P-sodium, MCPA, MCPA-butotyl, MCPA-dimethylammonium, MCPA-2-ethylhexyl, MCPA-potassium, MCPA-sodium, MCPA-thioethyl, MCPB, MCPB-ethyl, MCPB-sodium, mecoprop, mecoprop-butotyl, mecoprop-sodium, mecoprop-P, mecoprop-P-butotyl, mecoprop-P-dimethylammonium, mecoprop-P-2-ethylhexyl, mecoprop-P-potassium, naproanilide or clomeprop; an aromatic carboxylic acid type such as 2,3,6-TBA, dicamba, dicamba-butotyl, dicamba-diglycolamine, dicamba-dimethylammonium, dicamba-diolamine, dicamba-isopropylammonium, dicamba-potassium, dicamba-sodium, dichlobenil, picloram, picloram-dimethylammonium, picloram-isoctyl, picloram-potassium, picloram-triisopropanolammonium, picloram-triisopropylammonium, picloram-trolamine, triclopyr, triclopyr-butotyl, triclopyr-triethylammonium, clopyralid, clopyralid-olamine, clopyralid-potassium, clopyralid-triisopropanolammonium or aminopyralid; and others such as naptalam, naptalam-sodium, benazolin, benazolin-ethyl, quinclorac, quinmerac, diflufenzopyr, diflufenzopyr-sodium, fluroxypyr, fluroxypyr-2-butoxy-1-methylethyl, fluroxypyr-meptyl, chlorflurenol, chlorflurenol-methyl, aminocyclopyrachlor, aminocyclopyrachlor-methyl or aminocyclopyrachlor-potassium.

(2) Those which are believed to exhibit herbicidal effects by inhibiting photosynthesis of plants, such as a urea type such as chlorotoluron, diuron, fluometuron, linuron, isoproturon, metobenzuron, tebuthiuron, dimefuron, isouron, karbutilate, methabenzthiazuron, metoxuron, monolinuron, neburon, siduron, terbumeton, trietazine or metobromuron; a triazine type such as simazine, atrazine, atratone, simetryn, prometryn, dimethametryn, hexazinone, metribuzin, terbuthylazine, cyanazine, ametryn, cybutryne, triaziflam, indaziflam, terbutryn, propazine, metamitron or prometon; a uracil type such as bromacil, bromacyl-lithium, lenacil or terbacil; an anilide type such as propanil or cypromid; a carbamate type such as swep, desmedipham or phenmedipham; a hydroxybenzonitrile type such as bromoxynil, bromoxynil-octanoate, bromoxynil-heptanoate, ioxynil, ioxynil-octanoate, ioxynil-potassium or ioxynil-sodium; and others such as pyridate, bentazone, bentazone-sodium, amicarbazone, methazole or pentanochlor.

(3) Quaternary ammonium salt type such as paraquat or diquat, which is believed to be converted to free radicals by itself to form active oxygen in the plant body and shows rapid herbicidal efficacy.

(4) Those which are believed to exhibit herbicidal effects by inhibiting chlorophyll biosynthesis of plants and abnormally accumulating a photosensitizing peroxide substance in the plant body, such as a diphenylether type such as nitrofen, chlomethoxyfen, bifenox, acifluorfen, acifluorfen-sodium, fomesafen, fomesafen-sodium, oxyfluorfen, lactofen, aclonifen, ethoxyfen-ethyl (HC-252), fluoroglycofen-ethyl or fluoroglycofen; a cyclic imide type such as chlorphthalim; and others such as isopropazole or flupoxam.

(5) Those which are believed to exhibit herbicidal effects characterized by bleaching activities by inhibiting chromogenesis of plants such as carotenoids, such as a pyridazinone type such as norflurazon, chloridazon or metflurazon; a pyrazole type such as pyrazolynate, pyrazoxyfen, benzofenap, topramezone or pyrasulfotole; and others such as amitrole, fluridone, flurtamone, diflufenican, methoxyphenone, clomazone, sulcotrione, mesotrione, tembotrione, tefuryltrione (AVH-301), bicyclopyrone, isoxaflutole, difenzoquat, difenzoquat-metilsulfate, isoxachlortole, benzobicyclon, picolinafen, beflubutamid, a compound (SW-065, H-965) disclosed in the claim of WO2003/016286, a compound (KIH-3653, KUH-110) disclosed in the claim of WO2009/016841, a compound disclosed in the claim of WO2005/118530, a compound disclosed in the claim of WO2008/065907, or a compound disclosed in the claim of WO2009/142318.

(6) Those which exhibit strong herbicidal effects specifically to gramineous plants, such as an aryloxyphenoxypropionic acid type such as diclofop-methyl, diclofop, pyriphenop-sodium, fluazifop-butyl, fluazifop, fluazifop-P, fluazifop-P-butyl, haloxyfop-methyl, haloxyfop, haloxyfop-etotyl, haloxyfop-P, haloxyfop-P-methyl, quizalofop-ethyl, quizalofop-P, quizalofop-P-ethyl, quizalofop-P-tefuryl, cyhalofop-butyl, fenoxaprop-ethyl, fenoxaprop-P, fenoxaprop-P-ethyl, metamifop-propyl, metamifop, clodinafop-propargyl, clodinafop or propaquizafop; a cyclohexanedione type such as alloxydim-sodium, alloxydim, clethodim, sethoxydim, tralkoxydim, butroxydim, tepraloxydim, profoxydim or cycloxydim; and others such as flamprop-M-methyl, flamprop-M or flamprop-M-isopropyl.

(7) Those which are believed to exhibit herbicidal effects by inhibiting an amino acid biosynthesis of plants, such as a sulfonylurea type such as chlorimuron-ethyl, chlorimuron, sulfometuron-methyl, sulfometuron, primisulfuron-methyl, primisulfuron, bensulfuron-methyl, bensulfuron, chlorsulfuron, metsulfuron-methyl, metsulfuron, cinosulfuron, pyrazosulfuron-ethyl, pyrazosulfuron, azimsulfuron, rimsulfuron, nicosulfuron, imazosulfuron, cyclosulfamuron, prosulfuron, flupyrsulfuron-methyl-sodium, flupyrsulfuron, triflusulfuron-methyl, triflusulfuron, halosulfuron-methyl, halosulfuron, thifensulfuron-methyl, thifensulfuron, ethoxysulfuron, oxasulfuron, ethametsulfuron, ethametsulfuron-methyl, iodosulfuron, iodosulfuron-methyl-sodium, sulfosulfuron, triasulfuron, tribenuron-methyl, tribenuron, tritosulfuron, foramsulfuron, trifloxysulfuron, trifloxysulfuron-sodium, mesosulfuron-methyl, mesosulfuron, orthosulfamuron, flucetosulfuron, amidosulfuron, propyrisulfuron (TH-547), metazosulfuron, iofensulfuron, or a compound disclosed in the claim of EP0645386; a triazolopyrimidine-sulfonamide type such as flumetsulam, metosulam, diclosulam, cloransulam-methyl, florasulam, penoxsulam or pyroxsulam; an imidazolinone type such as imazapyr, imazapyr-isopropylammonium, imazethapyr, imazethapyr-ammonium, imazaquin, imazaquin-ammonium, imazamox, imazamox-ammonium, imazamethabenz, imazamethabenz-methyl or imazapic; a pyrimidinylsalicylic acid type such as pyrithiobac-sodium, bispyribac-sodium, pyriminobac-methyl, pyribenzoxim, pyriftalid or pyrimisulfan; a sulfonylaminocarbonyltriazolinone type such as flucarbazone, flucarbazone-sodium, propoxycarbazone-sodium, propoxycarbazone or thiencarbazone; and others such as glyphosate, glyphosate-sodium, glyphosate-potassium, glyphosate-ammonium, glyphosate-diammonium, glyphosate-isopropylammonium, glyphosate-trimesium, glyphosate-sesquisodium, glufosinate, glufosinate-ammonium, glufosinate-P, glufosinate-P-ammonium, glufosinate-P-sodium, bilanafos, bilanafos-sodium, cinmethylin or triafamone.

(8) Those which are believed to exhibit herbicidal effects by inhibiting cell mitoses of plants, such as a dinitroaniline type such as trifluralin, oryzalin, nitralin, pendimethalin, ethalfluralin, benfluralin, prodiamine, butralin or dinitramine; an amide type such as bensulide, napropamide, propyzamide or pronamide; an organic phosphorus type such as amiprofos-methyl, butamifos, anilofos or piperophos; a phenyl carbamate type such as propham, chlorpropham, barban or carbetamide; a cumylamine type such as daimuron, cumyluron, bromobutide or methyldymron; and others such as asulam, asulam-sodium, dithiopyr, thiazopyr, chlorthal-dimethyl, chlorthal or diphenamid.

(9) Those which are believed to exhibit herbicidal effects by inhibiting protein biosynthesis or lipid biosynthesis of plants, such as a chloroacetamide type such as alachlor, metazachlor, butachlor, pretilachlor, metolachlor, S-metolachlor, thenylchlor, pethoxamid, acetochlor, propachlor, dimethenamid, dimethenamid-P, propisochlor or dimethachlor; a thiocarbamate type such as molinate, dimepiperate, pyributicarb, EPTC, butylate, vernolate, pebulate, cycloate, prosulfocarb, esprocarb, thiobencarb, diallate, tri-allate or orbencarb; and others such as etobenzanid, mefenacet, flufenacet, tridiphane, cafenstrole, fentrazamide, oxaziclomefone, indanofan, benfuresate, pyroxasulfone, fenoxasulfone, dalapon, dalapon-sodium, TCA-sodium or trichloroacetic acid.

(10) MSMA, DSMA, CMA, endothall, endothall-dipotassium, endothall-sodium, endothall-mono(N,N-dimethylalkylammonium), ethofumesate, sodium chlorate, pelargonic acid (nonanoic acid), fosamine, fosamine-ammonium, pinoxaden, ipfencarbazone (HOK-201), aclolein, ammonium sulfamate, borax, chloroacetic acid, sodium chloroacete, cyanamide, methylarsonic acid, dimethylarsinic acid, sodium dimethylarsinate, dinoterb, dinoterb-ammonium, dinoterb-diolamine, dinoterb-acetate, DNOC, ferrous sulfate, flupropanate, flupropanate-sodium, isoxaben, mefluidide, mefluidide-diolamine, metam, metam-ammonium, metam-potassium, metam-sodium, methyl isothiocyanate, pentachlorophenol, sodium pentachlorophenoxide, pentachlorophenol laurate, quinoclamine, sulfuric acid, urea sulfate, methiozolin (MRC-01), etc.

(11) Those which are believed to exhibit herbicidal effects by being parasitic on plants, such as *Xanthomonas campestris*, *Epicoccosirus nematosorus*, *Epicoccosirus nematosperus*, *Exserohilum monoseras* or *Drechsrela monoceras*.

The herbicidal composition of the present invention may be prepared by mixing the compounds A and B, as active ingredients, with various agricultural additives in accordance with conventional formulation methods for agricultural chemicals, and applied in various formulations such as dusts, granules, water dispersible granules, wettable powders, tablets, pills, capsules (including a formulation packaged by a water soluble film), water-based suspensions, oil-based suspensions, microemulsions, suspoemulsions, water soluble powders, emulsifiable concentrates, soluble concentrates or pastes. It may be formed into any formulation which is commonly used in this field, so long as the object of the present invention is thereby met.

The type of the formulation of the herbicidal composition of the present invention is preferably a liquid formulation which can be applied as it is or a formulation to be applied after diluted with water, since by the formulation such that a solid formulation such as microgranules is applied as it is without being diluted with water, application to a wide area at once is difficult, and the application will take long. More specifically, water dispersible granules, wettable powders, water-based suspensions, oil-based suspensions, emulsifiable concentrates, soluble concentrates and the like are preferred.

At the time of the formulation, the compounds A and B may be mixed together for the formulation, or they may be separately formulated.

The additives to be used for the formulation include, for example, a solid carrier such as kaolinite, sericite, diatomaceous earth, slaked lime, calcium carbonate, talc, white carbon, kaoline, bentonite, clay, sodium carbonate, sodium bicarbonate, mirabilite, zeolite or starch; a solvent such as water, toluene, xylene, solvent naphtha, dioxane, dimethylsulfoxide, N,N-dimethylformamide, dimethylacetamide, N-methyl-2-pyrrolidone or an alcohol; an anionic surfactant such as a salt of fatty acid, a benzoate, a polycarboxylate, a salt of alkylsulfuric acid ester, an alkyl sulfate, an alkylaryl sulfate, an alkyl diglycol ether sulfate, a salt of alcohol sulfuric acid ester, an alkyl sulfonate, an alkylaryl sulfonate, an aryl sulfonate, a lignin sulfonate, an alkyldiphenylether disulfonate, a polystyrene sulfonate, a salt of alkylphosphoric acid ester, an alkylaryl phosphate, a styrylaryl phosphate, a salt of polyoxyethylene alkyl ether sulfuric acid ester, a polyoxyethylene alkylaryl ether sulfate, a salt of polyoxyethylene alkylaryl ether sulfuric acid ester, a polyoxyethylene alkyl ether phosphate, a salt of polyoxyethylene alkylaryl phosphoric acid ester, a salt of polyoxyethylene aryl ether phosphoric acid ester, a naphthalene sulfonic acid condensed with formaldehyde or a salt of alkylnaphthalene sulfonic acid condensed with formaldehyde; a nonionic surfactant such as a sorbitan fatty acid ester, a glycerin fatty acid ester, a fatty acid polyglyceride, a fatty acid alcohol polyglycol ether, acetylene glycol, acetylene alcohol, an oxyalkylene block polymer, a polyoxyethylene alkyl ether, a polyoxyethylene alkylaryl ether, a polyoxyethylene styrylaryl ether, a polyoxyethylene glycol alkyl ether, polyethylene glycol, a polyoxyethylene fatty acid ester, a polyoxyethylene sorbitan fatty acid ester, a polyoxyethylene glycerin fatty acid ester, a polyoxyethylene hydrogenated castor oil or a polyoxypropylene fatty acid ester; and a vegetable oil or mineral oil such as olive oil, kapok oil, castor oil, palm oil, *camellia* oil, coconut oil, sesame oil, corn oil, rice bran oil, peanut oil, cottonseed oil, soybean oil, rapeseed oil, linseed oil, tung oil or liquid paraffins; transesterified vegetable oil such as methylated rapeseed oil or ethylated rapeseed oil. These additives may suitably be selected for use alone or in combination as a mixture of two or more of them, so long as the object of the present invention is met. Further, additives other than the above-mentioned may be suitably selected for use among those known in this field. For example, various additives commonly used, such as a filler, a thickener, an anti-settling agent, an anti-freezing agent, a dispersion stabilizer, a safener, an anti-mold agent, a bubble agent, a disintegrator and a binder, may be used. The mix ratio by weight of the active ingredient to such various additives in the herbicidal composition of the present invention may be from 0.001:99.999 to 95:5, preferably from 0.005:99.995 to 90:10.

As a method of applying the herbicidal composition of the present invention, a proper method can be employed among various methods depending upon various conditions such as the application site, the type of the formulation, and the type and the growth stage of the undesired plants to be controlled, and for example, the following methods may be mentioned.

1. The compound A and the compound B are formulated together, and the formulation is applied as it is.
2. The compound A and the compound B are formulated together, the formulation is diluted to a predetermined concentration with e.g. water, and as the case requires, a spreader (such as a surfactant, a vegetable oil or a mineral oil) is added for application.
3. The compound A and the compound B are separately formulated and applied as they are.
4. The compound A and the compound B are separately formulated, and they are diluted to a predetermined concentration with e.g. water, and as the case requires, a spreader (such as a surfactant, a vegetable oil or a mineral oil) is added for application.
5. The compound A and the compound B are separately formulated, and the formulations are mixed when diluted to a predetermined concentration with e.g. water, and as the case requires, a spreader (such as a surfactant, a vegetable oil or a mineral oil) is added for application.

Now, preferred embodiments of the present invention will be described below. However, the present invention is by no means restricted thereto.

(1) A herbicidal composition comprising (A) flazasulfuron or its salt and (B) at least one protoporphyrinogen oxidase inhibitor selected from the group consisting of a phenylpyrazole compound, a triazolinone compound, a N-phenylphthalimide compound, a pyrimidindione compound, an oxadiazole compound, an oxazolidinedione compound, a thiadiazole compound, pyraclonil, profluazol, flufenpyr-ethyl and their salts.

(2) The compound according to the above (1), wherein (B) is at least one member selected from the group consisting of a phenylpyrazole compound, a triazolinone compound, a N-phenylphthalimide compound, a pyrimidindione compound, an oxadiazole compound and their salts.

(3) The compound according to the above (2), wherein (B) is at least one member selected from the group consisting of a phenylpyrazole compound, a triazolinone compound, a N-phenylphthalimide compound, a pyrimidindione compound and their salts.

(4) The compound according to the above (3), wherein (B) is at least one member selected from the group consisting of a phenylpyrazole compound, a triazolinone compound, a N-phenylphthalimide compound and their salts.

(5) The composition according to the above (1), wherein (B) is at least one member selected from the group consisting of pyraflufen-ethyl, fluazolate, azafenidin, bencarbazone, carfentrazone-ethyl, sulfentrazone, cinidon-ethyl, flumiclorac-pentyl, flumioxazin, benzfendizone, butafenacil, saflufenacil, ethyl [3-(2-chloro-4-fluoro-5-(3-methyl-2,6-dioxo-4-trifluoromethyl-3,6-dihydro-2H-pyrimidin-1-yl) phenoxy)pyridin-2-yloxy]acetate (test code: SYN-523), oxadiargyl, oxadiazon, pentoxazone, fluthiacet-methyl, thidiazimin, pyraclonil, profluazol, flufenpyr-ethyl and their salts.

(6) The composition according to the above (1), wherein (B) is at least one member selected from the group consisting of pyraflufen-ethyl, carfentrazone-ethyl, sulfentrazone, flumioxazin, saflufenacil, oxadiargyl, fluthiacet-methyl, flufenpyr-ethyl, butafenacil, pentoxazone, pyraclonil and their salts.

(7) The composition according to the above (1), wherein (B) is at least one member selected from the group consisting of pyraflufen-ethyl and carfentrazone-ethyl.

(8) The composition according to the above (1), wherein (B) is pyraflufen-ethyl.

(9) The composition according to the above (1), wherein (B) is carfentrazone-ethyl.

(10) The composition according to any one of the above (1) to (9), which contains synergistic herbicidally effective amounts of (A) and (B).

(11) The composition according to any one of the above (1) to (10), wherein the mixing ratio of (A) to (B) is from 100:1 to 1:100 by the weight ratio.

(12) A method for controlling undesired plants or inhibiting their growth, which comprises applying a herbicidally effective amount of a herbicidal composition comprising (A) flazasulfuron or its salt and (B) at least one protoporphyrinogen oxidase inhibitor selected from the group consisting of a phenylpyrazole compound, a triazolinone compound, an oxadiazole compound, an oxazolidinedione compound, a N-phenylphthalimide compound, a thiadiazole compound, a pyrimidindione compound, pyraclonil, profluazol, flufenpyr-ethyl and their salts, to the undesired plants or to a place where they grow.

(13) A method for controlling undesired plants or inhibiting their growth, which comprises applying herbicidally effective amounts of (A) flazasulfuron or its salt and (B) at least one protoporphyrinogen oxidase inhibitor selected from the group consisting of a phenylpyrazole compound, a triazolinone compound, an oxadiazole compound, an oxazolidinedione compound, a N-phenylphthalimide compound, a thiadiazole compound, a pyrimidindione compound, pyraclonil, profluazol, flufenpyr-ethyl and their salts, to the undesired plants or to a place where they grow.

(14) The method according to the above (12) or (13), wherein (B) is at least one member selected from the group consisting of pyraflufen-ethyl and carfentrazone-ethyl.

(15) The method according to the above (12) or (13), wherein (B) is pyraflufen-ethyl.

(16) The method according to the above (12) or (13), wherein (B) is carfentrazone-ethyl.

(17) The method according to the above (12) or (13), wherein synergistic herbicidally effective amounts of (A) and (B) are applied.

(18) The method according to the above (12) or (13), wherein (A) is applied in an amount of from 0.5 to 120 g/ha, and (B) is applied in an amount of from 0.5 to 1,000 g/ha.

(19) The method according to the above (12) or (13), wherein (A) is applied in an amount of from 10 to 100 g/ha, and (B) is applied in an amount of from 1 to 1,000 g/ha.

(20) The method according to the above (15), wherein (A) is applied in an amount of from 10 to 100 g/ha, and (B) is applied in an amount of from 5 to 80 g/ha.

(21) The method according to the above (16), wherein (A) is applied in an amount of from 10 to 100 g/ha, and (B) is applied in an amount of from 2.5 to 400 g/ha.

EXAMPLES

The present invention will be described in further detail with reference to Examples. However, it should be understood that the present invention is by no means restricted thereto.

Test Example 1

Upland field soil was put into a 1/1,000,000 ha pot, and seeds of persian speedwell (*Veronica persica* Poir.) were sown. When persian speedwell reached from 7 to 8 leaf-stage, water dispersible granules containing flazasulfuron as an active ingredient (tradename: SHIBAGEN DF, manufactured by Ishihara Sangyo Kaisha, Ltd.) and SC agent containing pyraflufen-ethyl as an active ingredient (tradename: ECOPART FLOWABLE, manufactured by NIHON NOYAKU CO., LTD.) in predetermined amounts were diluted with water (corresponding to 1,000 L/ha) containing 0.05 vol % of an agricultural adjuvant (tradename: KUSA-RINO, manufactured by NIHON NOYAKU CO., LTD.) and applied for foliar treatment by a small sprayer.

On the 21st day after the treatment, the state of growth of persian speedwell was visually observed and evaluated in accordance with the following evaluation standard. The growth inhibition rate (%) (measured value) and the growth inhibition rate (%) (calculated value) calculated in accordance with the Colby's formula are shown in Table 1.

Growth inhibition rate (%)=0 (equivalent to the non-treated area) to 100 (complete kill)

TABLE 1

| Active ingredient | Dose (g/ha) | Growth inhibition rate (%) of persian speedwell | |
|---|---|---|---|
| | | Measured value | Calculated value |
| Flazasulfuron | 25 | 10 | — |
| Pyraflufen-ethyl | 10 | 43 | — |
| Flazasulfuron + Pyraflufen-ethyl | 25 + 10 | 63 | 49 |

Test Example 2

Upland field soil was put into a 1/1,000,000 ha pot, and seeds of black nightshade (*Solanum nigrum* L.) were sown. When black nightshade reached from 3.2 to 3.5 leaf-stage, SHIBAGEN DF (tradename) and ECOPART FLOWABLE (tradename) in predetermined amounts were diluted with water (corresponding to 1,000 L/ha) containing 0.05 vol % of KUSARINO (tradename) and applied for foliar treatment by a small sprayer.

On the 21st day after the treatment, the state of growth of black nightshade was visually observed, and the growth inhibition rate (%) obtained in the same manner as in Test Example 1 is shown in Table 2.

TABLE 2

| Active ingredient | Dose (g/ha) | Growth inhibition rate (%) of black nightshade | |
|---|---|---|---|
| | | Measured value | Calculated value |
| Flazasulfuron | 50 | 74 | — |
| Pyraflufen-ethyl | 2.5 | 88 | — |
| Flazasulfuron + Pyraflufen-ethyl | 50 + 2.5 | 99 | 97 |

As shown in Table 2, in order to completely suppress growth of black nightshade with flazasulfuron alone, a dose of 50 g/ha or more is required. On the other hand, although not shown in the above Table, the growth inhibition rate of black nightshade was 100% (calculated value: 96%) when flazasulfuron (12.5 g/ha) and pyraflufen-ethyl (5 g/ha) were used in combination, and accordingly it was found that the total dose can be reduced to 17.5 g/ha by using the herbicidal composition of the present invention.

Test Example 3

Upland field soil was put into a 1/1,000,000 ha pot, and seeds of sticky chickweed (*Cerastium glomeratum* Thuill.) were sown. When sticky chickweed reached from 3.3 to 4.0 leaf-stage, SHIBAGEN DF (tradename) and ECOPART FLOWABLE (tradename) in predetermined amounts were diluted with water (corresponding to 1,000 L/ha) and applied for foliar treatment by a small sprayer.

On the 21st day after the treatment, the state of growth of sticky chickweed was visually observed, and the growth inhibition rate (%) obtained in the same manner as in Test Example 1 is shown in Table 3.

TABLE 3

| Active ingredient | Dose (g/ha) | Growth inhibition rate (%) of sticky chickweed | |
|---|---|---|---|
| | | Measured value | Calculated value |
| Flazasulfuron | 6.3 | 92 | — |
| Pyraflufen-ethyl | 10 | 58 | — |
| Flazasulfuron + Pyraflufen-ethyl | 6.3 + 10 | 99 | 97 |

Test Example 4

Upland field soil was put into a 1/1,000,000 ha pot, and seeds of common lambsquarters (*Chenopodium album* L.) were sown. When common lambsquarters reached from 6 to 7 leaf-stage, SHIBAGEN DF (tradename) and water dispersible granules containing carfentrazone-ethyl as an active ingredient (tradename: TASK DF, manufactured by Ishihara Sangyo Kaisha, Ltd.) in predetermined amounts were diluted with water (corresponding to 1,000 L/ha) and applied for foliar treatment by a small sprayer.

On the 21st day after the treatment, the state of growth of common lambsquarters was visually observed, and the growth inhibition rate (%) obtained in the same manner as in Test Example 1 is shown in Table 4.

TABLE 4

| Active ingredient | Dose (g/ha) | Growth inhibition rate (%) of lambsquarters | |
|---|---|---|---|
| | | Measured value | Calculated value |
| Flazasulfuron | 1.6 | 3 | — |
| Carfentrazone-ethyl | 27.4 | 92 | — |
| Flazasulfuron + Carfentrazone-ethyl | 1.6 + 27.4 | 96 | 92 |

Test Example 5

Upland field soil was put into a 1/300,000 ha pot, and seeds of wild oat (*Avena fatua* L.) were sown. One day later, SHIBAGEN DF (tradename), water dispersible granules containing saflufenacil as an active ingredient (tradename: Treevix, manufactured by BASF) and a wettable powder containing oxadiargyl (manufactured by SIGMA-ALDRICH) as an active ingredient prepared in accordance with a conventional preparation method, in predetermined amounts were diluted with water (corresponding to 300 L/ha) and applied for soil treatment by a small sprayer.

On the 13th day after the treatment, the state of growth of wild oat was visually observed, and the growth inhibition rate (%) obtained in the same manner as in Test Example 1 is shown in Table 5.

TABLE 5

| Active ingredient | Dose (g/ha) | Growth inhibition rate (%) of wild oat | |
|---|---|---|---|
| | | Measured value | Calculated value |
| Flazasulfuron | 25 | 40 | — |
| | 50 | 70 | — |

TABLE 5-continued

| Active ingredient | Dose (g/ha) | Growth inhibition rate (%) of wild oat | |
|---|---|---|---|
| | | Measured value | Calculated value |
| Saflufenacil | 25 | 15 | — |
| | 50 | 5 | — |
| Oxadiargyl | 50 | 5 | — |
| | 800 | 20 | — |
| Flazasulfuron + Saflufenacil | 25 + 25 | 70 | 49 |
| | 50 + 50 | 80 | 72 |
| Flazasulfuron + Oxadiargyl | 50 + 50 | 80 | 72 |
| | 25 + 800 | 78 | 52 |

Test Example 6

Upland field soil was put into a 1/300,000 ha pot, and seeds of *rostrate sesbania* (*Sesbania rostrata* Bremek. & Oberm.) were sown. One day later, SHIBAGEN DF (tradename), water dispersible granules containing flumioxazin as an active ingredient (tradename: Chateau, manufactured by Valent) and a wettable powder containing oxadiargyl (manufactured by SIGMA-ALDRICH) as an active ingredient prepared in accordance with a conventional preparation method, in predetermined amounts were diluted with water (corresponding to 300 L/ha) and applied for soil treatment by a small sprayer.

On the 28th day after the treatment, the state of growth of *rostrate sesbania* was visually observed, and the growth inhibition rate (%) obtained in the same manner as in Test Example 1 is shown in Table 6.

TABLE 6

| Active ingredient | Dose (g/ha) | Growth inhibition rate (%) of *rostrate sesbania* | |
|---|---|---|---|
| | | Measured value | Calculated value |
| Flazasulfuron | 12.5 | 25 | — |
| Flumioxazin | 250 | 70 | — |
| Oxadiargyl | 400 | 20 | — |
| Flazasulfuron + Flumioxazin | 12.5 + 250 | 95 | 78 |
| Flazasulfuron + Oxadiargyl | 12.5 + 400 | 65 | 40 |

Test Example 7

Upland field soil was put into a 1/300,000 ha pot, and seeds of sunn-hemp (*Crotalaria juncea* L.) were sown. One day later, SHIBAGEN DF (tradename), ECOPART FLOWABLE (tradename) and a wettable powder containing oxadiargyl (manufactured by SIGMA-ALDRICH) as an active ingredient prepared in accordance with a conventional preparation method, in predetermined amounts were diluted with water (corresponding to 300 L/ha) and applied for soil treatment by a small sprayer.

On the 28th day after the treatment, the state of growth of sunn-hemp was visually observed, and the growth inhibition rate (%) obtained in the same manner as in Test Example 1 is shown in Table 7.

TABLE 7

| Active ingredient | Dose (g/ha) | Growth inhibition rate (%) of sunn-hemp | |
|---|---|---|---|
| | | Measured value | Calculated value |
| Flazasulfuron | 50 | 55 | — |
| Pyraflufen-ethyl | 10 | 20 | — |
| | 50 | 45 | — |
| Oxadiargyl | 400 | 40 | — |
| Flazasulfuron + Pyraflufen-ethyl | 50 + 10 | 70 | 64 |
| | 50 + 50 | 85 | 75 |
| Flazasulfuron + Oxadiargyl | 50 + 400 | 78 | 73 |

Test Example 8

Upland field soil was put into a 1/300,000 ha pot, and seeds of velvetleaf (*Abutilon theophrasti* Medic.) were sown. One day later, SHIBAGEN DF (tradename), water dispersible granules containing sulfentrazone as an active ingredient (tradename: Authority, manufactured by FMC Corporation) and Treevix (tradename) in predetermined amounts were diluted with water (corresponding to 300 L/ha) and applied for soil treatment by a small sprayer.

On the 28th day after the treatment, the state of growth of velvetleaf was visually observed, and the growth inhibition rate (%) obtained in the same manner as in Test Example 1 is shown in Table 8.

TABLE 8

| Active ingredient | Dose (g/ha) | Growth inhibition rate (%) of velvetleaf | |
|---|---|---|---|
| | | Measured value | Calculated value |
| Flazasulfuron | 50 | 88 | — |
| | 100 | 88 | — |
| Sulfentrazone | 25 | 20 | — |
| Saflufenacil | 5 | 0 | — |
| | 10 | 65 | — |
| Flazasulfuron + Sulfentrazone | 50 + 25 | 100 | 90 |
| Flazasulfuron + Saflufenacil | 50 + 5 | 100 | 88 |
| | 100 + 10 | 100 | 96 |

Test Example 9

Upland field soil was put into a 1/300,000 ha pot, and seeds of black nightshade (*Solanum nigrum* L.) were sown. One day later, SHIBAGEN DF (tradename) and Chateau (tradename) in predetermined amounts were diluted with water (corresponding to 300 L/ha) and applied for soil treatment by a small sprayer.

On the 28th day after the treatment, the state of growth of black nightshade was visually observed, and the growth inhibition rate (%) obtained in the same manner as in Test Example 1 is shown in Table 9.

TABLE 9

| Active ingredient | Dose (g/ha) | Growth inhibition rate (%) of black nightshade | |
|---|---|---|---|
| | | Measured value | Calculated value |
| Flazasulfuron | 50 | 85 | — |
| Flumioxazin | 2.5 | 0 | — |

TABLE 9-continued

| Active ingredient | Dose (g/ha) | Growth inhibition rate (%) of black nightshade | |
|---|---|---|---|
| | | Measured value | Calculated value |
| Flazasulfuron + Flumioxazin | 50 + 2.5 | 90 | 85 |

Test Example 10

Upland field soil was put into a 1/1,000,000 ha pot, and seeds of bermudagrass (*Cynodon dactylon* (L.) Pers.) were sown. When bermudagrass reached from 2.2 to 2.5 leaf-stage, SHIBAGEN DF (tradename), TASK DF (tradename), Authority (tradename) and Chateau (tradename) in predetermined amounts were diluted with water (corresponding to 300 L/ha) containing 0.2 vol % of KUSARINO (tradename) and applied for foliar treatment by a small sprayer.

On the 28th day after the treatment, the state of growth of bermudagrass was visually observed, and the growth inhibition rate (%) obtained in the same manner as in Test Example 1 is shown in Table 10.

TABLE 10

| Active ingredient | Dose (g/ha) | Growth inhibition rate (%) of bermudagrass | |
|---|---|---|---|
| | | Measured value | Calculated value |
| Flazasulfuron | 50 | 75 | — |
| | 100 | 75 | — |
| Carfentrazone-ethyl | 20 | 0 | — |
| | 50 | 0 | — |
| Sulfentrazone | 50 | 30 | — |
| Flumioxazin | 5 | 20 | — |
| Flazasulfuron + Carfentrazone-ethyl | 50 + 50 | 85 | 75 |
| | 100 + 20 | 88 | 75 |
| Flazasulfuron + Sulfentrazone | 100 + 50 | 90 | 83 |
| Flazasulfuron + Flumioxazin | 100 + 5 | 88 | 80 |

Test Example 11

Upland field soil was put into a 1/1,000,000 ha pot, and seeds of bermudagrass (*Cynodon dactylon* (L.) Pers.) were sown. When bermudagrass reached from 3.8 to 4.3 leaf-stage, SHIBAGEN DF (tradename) and ECOPART FLOWABLE (tradename) in predetermined amounts were diluted with water (corresponding to 300 L/ha) containing 0.2 vol % of KUSARINO (tradename) and applied for foliar treatment by a small sprayer.

On the 28th day after the treatment, the state of growth of bermudagrass was visually observed, and the growth inhibition rate (%) obtained in the same manner as in Test Example 1 is shown in Table 11.

TABLE 11

| Active ingredient | Dose (g/ha) | Growth inhibition rate (%) of bermudagrass | |
|---|---|---|---|
| | | Measured value | Calculated value |
| Flazasulfuron | 12.5 | 15 | — |
| Pyraflufen-ethyl | 40 | 0 | — |

TABLE 11-continued

| Active ingredient | Dose (g/ha) | Growth inhibition rate (%) of bermudagrass | |
|---|---|---|---|
| | | Measured value | Calculated value |
| Flazasulfuron + Pyraflufen-ethyl | 12.5 + 40 | 60 | 15 |

Test Example 12

Upland field soil was put into a 1/1,000,000 ha pot, and seeds of persian speedwell (*Veronica persica* Poir.) were sown. When persian speedwell reached from 4.0 to 4.3 leaf-stage, SHIBAGEN DF (tradename), ECOPART FLOWABLE (tradename) and TASK DF (tradename) in predetermined amounts were diluted with water (corresponding to 300 L/ha) containing 0.2 vol % of KUSARINO (tradename) and applied for foliar treatment by a small sprayer.

On the 28th day after the treatment, the state of growth of persian speedwell was visually observed, and the growth inhibition rate (%) obtained in the same manner as in Test Example 1 is shown in Table 12.

TABLE 12

| Active ingredient | Dose (g/ha) | Growth inhibition rate (%) of persian speedwell | |
|---|---|---|---|
| | | Measured value | Calculated value |
| Flazasulfuron | 25 | 0 | — |
| Pyraflufen-ethyl | 80 | 80 | — |
| Carfentrazone-ethyl | 25 | 65 | — |
| Flazasulfuron + Pyraflufen-ethyl | 25 + 80 | 100 | 80 |
| Flazasulfuron + Carfentrazone-ethyl | 25 + 25 | 85 | 65 |

Test Example 13

Upland field soil was put into a 1/300,000 ha pot, and seeds of japanese millet (*Echinochloa esculenta* (A. Braun) H. Scholz.) were sown. One day later, SHIBAGEN DF (tradename), a SC agent containing pyraclonil as an active ingredient (tradename: PYRACLON FLOWABLE, manufactured by Kyoyu Agri Co., Ltd.) and a SC agent containing pentoxazone as an active ingredient (tradename: WECHSER FLOWABLE, manufactured by MITSUI CHEMICALS AGRO, INC.) in predetermined amounts were diluted with water (corresponding to 300 L/ha) and applied for soil treatment by a small sprayer.

On the 14th day after the treatment, the state of growth of japanese millet was visually observed, and the growth inhibition rate (%) obtained in the same manner as in Test Example 1 is shown in Table 13.

TABLE 13

| Active ingredient | Dose (g/ha) | Growth inhibition rate (%) of japanese millet | |
|---|---|---|---|
| | | Measured value | Calculated value |
| Flazasulfuron | 50 | 80 | — |
| Pyraclonil | 100 | 30 | — |

TABLE 13-continued

| Active ingredient | Dose (g/ha) | Growth inhibition rate (%) of japanese millet | |
|---|---|---|---|
| | | Measured value | Calculated value |
| Pentoxazone | 100 | 0 | — |
| Flazasulfuron + Pyraclonil | 50 + 100 | 95 | 86 |
| Flazasulfuron + Pentoxazone | 50 + 100 | 90 | 80 |

Test Example 14

Upland field soil was put into a 1/300,000 ha pot, and seeds of *rostrate sesbania* (*Sesbania rostrata* Bremek. & Oberm.) were sown. One day later, SHIBAGEN DF (tradename), Chateau (tradename), a wettable powder containing flufenpyr-ethyl (manufactured by Wako Pure Chemical Industries, Ltd.) as an active ingredient prepared in accordance with a conventional preparation method, and water dispersible granules containing fluthiacet-methyl as an active ingredient (tradename: Cadet, manufactured by FMC Corporation) in predetermined amounts were diluted with water (corresponding to 300 L/ha) and applied for soil treatment by a small sprayer.

On the 14th day after the treatment, the state of growth of *rostrate sesbania* was visually observed, and the growth inhibition rate (%) obtained in the same manner as in Test Example 1 is shown in Table 14.

TABLE 14

| Active ingredient | Dose (g/ha) | Growth inhibition rate (%) of *rostrate sesbania* | |
|---|---|---|---|
| | | Measured value | Calculated value |
| Flazasulfuron | 50 | 50 | — |
| Flumioxazin | 200 | 75 | — |
| Flufenpyr-ethyl | 5 | 0 | — |
| Fluthiacet-methyl | 5 | 0 | — |
| Flazasulfuron + Flumioxazin | 50 + 200 | 99 | 88 |
| Flazasulfuron + Flufenpyr-ethyl | 50 + 5 | 70 | 50 |
| Flazasulfuron + Fluthiacet-methyl | 50 + 5 | 100 | 50 |

Test Example 15

Upland field soil was put into a 1/300,000 ha pot, and seeds of sunn-hemp (*Crotalaria juncea* L.) were sown. One day later, SHIBAGEN DF (tradename), Authority (tradename), Chateau (tradename), a wettable powder containing flufenpyr-ethyl (manufactured by Wako Pure Chemical Industries, Ltd.) as an active ingredient prepared in accordance with a conventional preparation method, and Cadet (tradename) in predetermined amounts were diluted with water (corresponding to 300 L/ha) and applied for soil treatment by a small sprayer.

On the 28th day after the treatment, the state of growth of sunn-hemp was visually observed, and the growth inhibition rate (%) obtained in the same manner as in Test Example 1 is shown in Table 15.

TABLE 15

| Active ingredient | Dose (g/ha) | Growth inhibition rate (%) of sunn-hemp | |
|---|---|---|---|
| | | Measured value | Calculated value |
| Flazasulfuron | 25 | 0 | — |
| Sulfentrazone | 500 | 30 | — |
| Flumioxazin | 100 | 0 | — |
| Flufenpyr-ethyl | 50 | 0 | — |
| Fluthiacet-methyl | 50 | 0 | — |
| Flazasulfuron + Sulfentrazone | 25 + 500 | 100 | 30 |
| Flazasulfuron + Flumioxazin | 25 + 100 | 70 | 0 |
| Flazasulfuron + Flufenpyr-ethyl | 25 + 50 | 90 | 0 |
| Flazasulfuron + Fluthiacet-methyl | 25 + 50 | 80 | 0 |

Test Example 16

Upland field soil was put into a 1/300,000 ha pot, and seeds of wild oat (*Avena fatua* L.) were sown. One day later, SHIBAGEN DF (tradename), Chateau (tradename), Treevix (tradename), PYRACLON FLOWABLE (tradename) and WECHSER FLOWABLE (tradename) in predetermined amounts were diluted with water (corresponding to 300 L/ha) and applied for soil treatment by a small sprayer.

On the 28th day after the treatment, the state of growth of wild oat was visually observed, and the growth inhibition rate (%) obtained in the same manner as in Test Example 1 is shown in Table 16.

TABLE 16

| Active ingredient | Dose (g/ha) | Growth inhibition rate (%) of wild oat | |
|---|---|---|---|
| | | Measured value | Calculated value |
| Flazasulfuron | 12.5 | 20 | — |
| | 25 | 75 | — |
| Flumioxazin | 250 | 90 | — |
| Saflufenacil | 50 | 0 | — |
| Pyraclonil | 250 | 40 | — |
| Pentoxazone | 250 | 0 | — |
| Flazasulfuron + Flumioxazin | 12.5 + 250 | 100 | 92 |
| Flazasulfuron + Saflufenacil | 12.5 + 50 | 70 | 20 |
| Flazasulfuron + Pyraclonil | 25 + 250 | 90 | 85 |
| Flazasulfuron + Pentoxazone | 25 + 250 | 80 | 75 |

Test Example 17

Upland field soil was put into a 1/300,000 ha pot, and seeds of wild oat (*Avena fatua* L.) were sown. One day later, SHIBAGEN DF (tradename) and Chateau (tradename) in predetermined amounts were diluted with water (corresponding to 300 L/ha) and applied for soil treatment by a small sprayer.

On the 14th day after the treatment, the state of growth of wild oat was visually observed, and the growth inhibition rate (%) obtained in the same manner as in Test Example 1 is shown in Table 17.

TABLE 17

| Active ingredient | Dose (g/ha) | Growth inhibition rate (%) of wild oat | |
|---|---|---|---|
| | | Measured value | Calculated value |
| Flazasulfuron | 25 | 30 | — |
| Flumioxazin | 500 | 75 | — |
| Flazasulfuron + Flumioxazin | 25 + 500 | 90 | 83 |

Test Example 18

Upland field soil was put into a 1/300,000 ha pot, and seeds of corn (*Zea mays* L.) were sown. One day later, SHIBAGEN DF (tradename) and a wettable powder containing butafenacil (synthesized by Ishihara Sangyo Kaisha, Ltd.) as an active ingredient prepared in accordance with a conventional preparation method, in predetermined amounts were diluted with water (corresponding to 300 L/ha) and applied for soil treatment by a small sprayer.

On the 14th day after the treatment, the state of growth of corn was visually observed, and the growth inhibition rate (%) obtained in the same manner as in Test Example 1 is shown in Table 18.

TABLE 18

| Active ingredient | Dose (g/ha) | Growth inhibition rate (%) of corn | |
|---|---|---|---|
| | | Measured value | Calculated value |
| Flazasulfuron | 12.5 | 70 | — |
| Butafenacil | 100 | 20 | — |
| Flazasulfuron + Butafenacil | 12.5 + 100 | 83 | 76 |

Test Example 19

Upland field soil was put into a 1/300,000 ha pot, and seeds of ivy-leaved morningglory (*Ipomoea hederacea* Jacq.) were sown. One day later, SHIBAGEN DF (tradename) and a wettable powder containing butafenacil (synthesized by Ishihara Sangyo Kaisha, Ltd.) as an active ingredient prepared in accordance with a conventional preparation method, in predetermined amounts were diluted with water (corresponding to 300 L/ha) and applied for soil treatment by a small sprayer.

On the 14th day after the treatment, the state of growth of ivy-leaved morningglory was visually observed, and the growth inhibition rate (%) obtained in the same manner as in Test Example 1 is shown in Table 19.

TABLE 19

| Active ingredient | Dose (g/ha) | Growth inhibition rate (%) of ivy-leaved morningglory | |
|---|---|---|---|
| | | Measured value | Calculated value |
| Flazasulfuron | 50 | 60 | — |
| Butafenacil | 10 | 0 | — |
| Flazasulfuron + Butafenacil | 50 + 10 | 85 | 60 |

Test Example 20

Upland field soil was put into a 1/300,000 ha pot, and seeds of shattercane (*Sorghum bicolor* (L.) Moench) were sown. One day later, SHIBAGEN DF (tradename) and Treevix (tradename) in predetermined amounts were diluted with water (corresponding to 300 L/ha) and applied for soil treatment by a small sprayer.

On the 14th day after the treatment, the state of growth of shattercane was visually observed, and the growth inhibition rate (%) obtained in the same manner as in Test Example 1 is shown in Table 20.

TABLE 20

| Active ingredient | Dose (g/ha) | Growth inhibition rate (%) of shattercane | |
|---|---|---|---|
| | | Measured value | Calculated value |
| Flazasulfuron | 12.5 | 0 | — |
| Saflufenacil | 100 | 20 | — |
| Flazasulfuron + Saflufenacil | 12.5 + 100 | 98 | 20 |

INDUSTRIAL APPLICABILITY

According to the present invention, it is possible to provide a herbicidal composition which has a broad herbicidal spectrum and also has a high activity and a long-lasting effect.

The entire disclosure of Japanese Patent Application No. 2011-087546 filed on Apr. 11, 2011 including specification, claims and summary is incorporated herein by reference in its entirety.

What is claimed is:

1. A method for controlling an undesired plant or inhibiting growth of an undesired plant, which comprises applying a herbicidally effective amount of a herbicidal composition comprising (A) flazasulfuron or its salt and (B) flumioxazin or its salt, to the undesired plant or to a place where the undesired plant grows, wherein the undesired plant is goosegrass, annual bluegrass, guinea grass, fall panicum, corn speedwell, hairy fleabane, horseweed, dandelion, rostrate sesbania, sesbania pea, white clover, sticky chickweed, garden spurge, threeseeded copperleaf, fireplant, carolina geranium, henbit, field Bindweed, or common purslane, wherein the mixing ratio is from 20:1 to 1:20 by weight ratio, and the composition presenting a synergistic herbicidal effect and combination of the (A) and (B) in the composition presenting a synergistic effect.

2. The method according to claim 1, wherein the undesired plant annual bluegrass, field Bindweed, or rostrate sesbania.

3. The method according to claim 1, further comprising applying at least one of pyraflufen-ethyl, carfentrazone-ethyl, sulfentrazone, oxadiargyl, fluthiacet-methyl, flufenpyr-ethyl, butafenacil, pentoxazone, and pyraclonil, and their salts, to the undesired plant or to the place where the undesired plant grows.

4. A method for controlling an undesired plant or inhibiting growth of an undesired plant, which comprises applying herbicidally effective amounts of (A) flazasulfuron or its salt and (B) flumioxazin or its salt, to the undesired plant or to a place where the undesired plant grows, wherein the undesired plant is goosegrass, annual bluegrass, guinea grass, fall panicum, corn speedwell, hairy fleabane, horseweed, dandelion, rostrate sesbania, sesbania pea, white clover, sticky chickweed, garden spurge, threeseeded copperleaf, fireplant, caroling geranium, henbit, field Bindweed, or common purslane, wherein the mixing ratio of (A) to (B) is from 20:1 to 1:20 by weight ratio, and combination of the (A) and (B) presenting a synergistic herbicidal effect.

5. The method according to claim 4, wherein the undesired plant is annual bluegrass, field Bindweed, or rostrate sesbania.

6. The method according to claim 4, further comprising applying at least one of pyraflufen-ethyl, carfentrazone-ethyl, sulfentrazone, oxadiargyl, fluthiacet-methyl, flufenpyr-ethyl, butafenacil, pentoxazone, and pyraclonil, and their salts, to the undesired plant or to the place where the undesired plant grows.

* * * * *

UNITED STATES PATENT AND TRADEMARK OFFICE
CERTIFICATE OF CORRECTION

PATENT NO.         : 9,743,666 B2
APPLICATION NO.    : 15/204566
DATED              : August 29, 2017
INVENTOR(S)        : R. Yamada et al.

Page 1 of 1

It is certified that error appears in the above-identified patent and that said Letters Patent is hereby corrected as shown below:

At Column 24, Line 53 (Claim 2, Line 2), insert --is-- before "annual".

Signed and Sealed this
Sixth Day of March, 2018

Andrei Iancu
*Director of the United States Patent and Trademark Office*